(12) United States Patent
Heider et al.

(10) Patent No.: US 6,423,454 B1
(45) Date of Patent: Jul. 23, 2002

(54) LITHIUM FLUOROALKYLPHOSPHATES AND THEIR USE AS ELECTROLYTE SALTS

(75) Inventors: Udo Heider, Riedstadt; Michael Schmidt, Weiterstadt; Peter Sartori, Rheinberg; Andreas Kühner, Darmstadt; Nikolai Ignatyev, Duisburg, all of (DE)

(73) Assignee: Merck Patent Gesellschaft mit beschrankter Haftung (DE)

( * ) Notice: Subject to any disclaimer, the term of this patent is extended or adjusted under 35 U.S.C. 154(b) by 0 days.

(21) Appl. No.: 09/572,939

(22) Filed: May 18, 2000

(30) Foreign Application Priority Data

Feb. 25, 2000 (DE) .......................................... 100 08 955

(51) Int. Cl.$^7$ ............................................. H01M 10/40
(52) U.S. Cl. ........................ 429/345; 429/199; 252/62.2
(58) Field of Search ................................. 429/199, 345; 252/62.2

(56) References Cited

U.S. PATENT DOCUMENTS 6,210,830 B1 * 4/2001 Sartori et al. ............... 429/199

* cited by examiner

Primary Examiner—Carol Chaney
(74) Attorney, Agent, or Firm—Millen, White, Zelano & Branigan, P.C.

(57) ABSTRACT

The present invention relates to lithium fluoroalkylphosphates, a process for preparing them and their use as electrolyte salts in batteries, capacitors, supercapacitors and electrolytic cells.

26 Claims, No Drawings

LITHIUM FLUOROALKYLPHOSPHATES AND THEIR USE AS ELECTROLYTE SALTS

The present invention relates to lithium fluoroalkylphosphates, a process for preparing them and their use as electrolyte salts in batteries, capacitors, supercapacitors and electrolytic cells.

The spread of portable electronic appliances such as laptop and palmtop computers, mobile telephones and video cameras, and thus also the need for light and powerful batteries has increased dramatically world-wide in recent years.

In view of this jump in the demand for batteries and the associated ecological problems, the development of rechargeable batteries having a long life is steadily increasing in importance.

Since the early 1990s, rechargeable lithium ion batteries have been commercially available. Most of these lithium ion batteries employ lithium hexafluorophosphate as electrolyte salt. However, this lithium salt is an extremely hydrolysis-sensitive compound having a low thermal stability, so that the corresponding lithium batteries can, owing to this property of the salt, only be produced by very complicated and thus also very costly methods.

The sensitivity of this lithium salt also reduces the life and the performance of these lithium batteries and also impairs their use under extreme conditions, e.g. at high temperatures.

There has therefore been no lack of attempts to provide lithium salts having improved properties. Thus, U.S. Pat. Nos. 4,505,997 and 9,202,966 describe the use of lithium bis(trifluoromethylsulfonyl)imide and lithium tris(trifluoromethylsulfonyl)methanide salts as electrolyte salts in batteries. Both salts display high anodic stability and form solutions having a high conductivity with organic carbonates. However, lithium bis(tri-fluoromethylsulfonyl)imide has the disadvantage that it does not sufficiently passivate the aluminium metal which functions as cathodic terminal lead in lithium batteries.

Lithium tris(trifluoromethylsulfonyl)methanide, on the other hand, is very expensive to produce and purify, so that the use of this salt as electrolyte salt in batteries greatly increases the production costs for such lithium batteries.

DE 196 411 38 teaches the use of lithium fluorophosphates preferably having perfluorinated or partially fluorinated ethyl and isopropyl groups as ligands. Although the thermal stability and the hydrolysis resistance of these lithium salts are significantly higher than those of lithium hexafluorophosphate, they hydrolyse within days in the presence of small traces of water, so that when using these electrolyte salts, too, the performance and life of the batteries based on these salts are reduced.

It is therefore an object of the invention to provide electrolyte salts which display no or only very slight signs of hydrolysis over a long period of time. A further object of the invention is to extend or improve the life and the performance of batteries, capacitors, supercapacitors and electrolytic cells.

This object is surprisingly achieved by the provision of lithium fluoroalkylphosphates of the general formula (I), $$\text{Li}^+[\text{PF}_x(\text{C}_y\text{F}_{2y+1-z}\text{H}_z)_{6-x}]^- \quad (I)$$

where
$1 \leq x \leq 5$
$3 \leq y \leq 8$ and
$0 \leq z \leq 2y+1$ and the ligands $(\text{C}_y\text{F}_{2y+1-z}\text{H}_z)$ can be identical or different, with the exception of compounds of the general formula (I')

$$\text{Li}^+[\text{PF}_a(\text{CH}_b\text{F}_c(\text{CF}_3)_d)_e]^- \quad (I')$$

in which a is an integer from 2 to 5, b=0 or 1, c=0 or 1, d=2 and e is an integer from 1 to 4, with the provisos that b and c are not simultaneously 0 and the sum of a+e is 6 and the ligands $(\text{CH}_b\text{F}_c(\text{CF}_3)_d)$ can be identical or different.

Preference is given to lithium fluoroalkylphosphates of the general formula (I) in which $1 \leq x \leq 5$, $3 \leq y \leq 8$ and $z=0$.

Particular preference is given to the following lithium fluoroalkylphosphates of the general formulae (I):

$$\text{Li}^+[\text{F}_{6-x}\text{P}(\text{CF}_2-\text{CF}_2-\text{CF}_3)_x]^-$$

and $$\text{Li}^+[\text{F}_{6-x}\text{P}(\text{CF}_2-\text{CF}_2-\text{CF}_2-\text{CF}_3)_x]^-$$

in which $1 \leq x \leq 3$ in each case.

The lithium fluoroalkylphosphates of the general formula (I) can be used, either in pure form or in the form of their mixtures, as electrolyte salts in primary and secondary batteries, capacitors, supercapacitors and electrolytic cells. It is also possible to use the lithium fluoroalkylphosphates of the invention together with further lithium salts known to those skilled in the art as electrolyte salt. The lithium fluoroalkylphosphates of the invention are preferably used in pure form as electrolyte salt, since particularly good reproducibility of the electrochemical properties can be achieved in this way.

The invention likewise provides a process for preparing the novel lithium fluoroalkylphosphates of the general formula (I), which is characterised in that at least one compound of the general formula $$\text{H}_m\text{P}(\text{C}_n\text{H}_{2n+1})_{3-m} \quad (III),$$

$$\text{OP}(\text{C}_n\text{H}_{2n+1})_3 \quad (IV),$$

$$\text{Cl}_m\text{P}(\text{C}_n\text{H}_{2n+1})_{3-m} \quad (V),$$

$$\text{F}_m\text{P}(\text{C}_n\text{H}_{2n+1})_{3-m} \quad (VI),$$

$$\text{Cl}_o\text{P}(\text{C}_n\text{H}_{2n+1})_{5-o} \quad (VII)$$

or $$\text{F}_o\text{P}(\text{C}_n\text{H}_{2n+1})_{5-o} \quad (VIII),$$

where in each case
$0 \leq m \leq 2$
$3 \leq n \leq 8$ and
$0 \leq o \leq 4$, is fluorinated by electrolysis in hydrogen fluoride, the resulting mixture of fluorination products is fractionated by extraction, phase separation and/or distillation, preferably by fractional distillation, and the resulting fluorinated alkylphosphorane is reacted with lithium fluoride in an aprotic solvent or solvent mixture in the absence of moisture, and the resulting novel lithium fluoroalkylphosphate of the general formula (I) is purified and isolated by customary methods.

The electrolysis is preferably carried out at a temperature of from −20 to +40° C., particularly preferably from −10 to +10° C. and very particularly preferably at from −5 to +5° C.; the pressure is preferably from 0.5 to 3 bar, particularly preferably from 0.5 to 1.5 bar and very particularly preferably atmospheric pressure.

The applied voltage during the electrolysis is preferably from 4 to 6 V, particularly preferably from 4.5 to 5.5 V, and the current density is preferably from 0.2 to 5 A/dm², particularly preferably from 0.2 to 2 A/dm² and very particularly preferably from 0.5 to 1.5 A/dm².

The compounds of the general formulae (V) and (VII) can also be reacted with inorganic fluorinating agents, preferably with $SbF_3$, $SbF_5$, $MoF_5$, $VF_5$ or mixtures thereof so as to replace the chlorine atoms by fluorine atoms prior to the electrolysis in hydrogen fluoride. The reaction conditions under which these fluorinations are carried out are known to those skilled in the art.

The reaction of the fluorinated alkylphosphorane with lithium fluoride is preferably carried out at a temperature of from −35 to 60° C., particularly preferably from −20 to +50° C. and very particularly preferably from −10 to 25° C.

Solvents used for the reaction of the fluorinated alkylphosphoranes with lithium fluoride are preferably carbonates, nitrites, ethers, esters, amides, sulfones or mixtures thereof.

Particular preference is given to using solvents or solvent mixtures which are suitable for direct use in a primary or secondary battery, a capacitor, a supercapacitor or an electrolytic cell, for example dimethyl carbonate, diethyl carbonate, propylene carbonate, ethylene carbonate, ethyl methyl carbonate, methyl propyl carbonate, 1,2-dimethoxyethane, 1,2-diethoxyethane, methyl acetate, y-butyrolactone, ethyl acetate, methyl propionate, ethyl propionate, methyl butyrate, ethyl butyrate, dimethylsulfoxide, dioxolane, sulfolane, acetonitrile, acrylonitrile, tetrahydrofuran, 2-methyltetrahydrofuran or mixtures thereof. The electrolytes obtained in this way are suitable for use in primary batteries, secondary batteries, capacitors, supercapacitors and electrolytic cells and are likewise provided by the present invention.

The concentration of the lithium fluoroalkylphosphate(s) of the invention in these electrolytes is preferably from 0.01 to 3 mol/l, particularly preferably from 0.01 to 2 mol/l and very particularly preferably from 0.1 to 1.5 mol/l.

The invention also provides primary batteries, secondary batteries, capacitors, supercapacitors and electrolytic cells containing at least one novel lithium fluoroalkylphosphate of the general formula (I) and, if desired, further lithium salts and/or additives. These further lithium salts and additives are known to those skilled in the art, for example from Doron Aurbach, Nonaqueous Electrochemistry, Marc Dekker Inc., New York 1999; D. Linden, Handbook of Batteries, Second Edition, McGraw-Hill Inc., New York 1995 and G. Mamantov and A. I. Popov, Chemistry of Nonaqueous Solutions, Current Progress, VCH Verlagsgemeinschaft, Weinheim 1994. They are hereby incorporated by reference into the present disclosure. The lithium fluoroalkylphosphates of the invention can be used with customary electrolytes. Examples of suitable electrolytes are those comprising electrolyte salts selected from the group consisting of $LiPF_6$, $LiBF_4$, $LiClO_4$, $LiAsF_6$, $LiCF_3SO_3$, $LiN(CF_3SO_2)_2$ or LiC$(CFSO_2)_3$ mixtures thereof. The electrolytes may further comprise organic isocyanates (DE 199 44 603) to reduce the water content. Likewise, the electrolytes may further comprise organic alkali metal salts (DE 199 10 968) as additives. Suitable alkali metal salts are alkali metal borates of the general formula $$Li^+B^-(OR^1)_m(OR^2)_p$$

where m and p are 0, 1, 2, 3 or 4 with m+p 4 and
$R^1$ and $R^2$ are identical or different, if desired are joined directly to one another by a single or double bond, and are, in each case individually or together, an aromatic or aliphatic carboxylic, dicarboxylic or sulfonic acid group, or are, in each case individually or together, an aromatic ring selected from the group consisting of phenyl, naphthyl, anthracenyl and phenanthrenyl, which may be unsubstituted or monosubstituted to tetrasubstituted by A or Hal, or are, in each case individually or together, a heterocyclic aromatic ring selected from the group consisting of pyridyl, pyrazyl and bipyridyl, which may be unsubstituted or monosubstituted to trisubstituted by A or Hal, or are, in each case individually or together, an aromatic hydroxy acid selected from the group consisting of aromatic hydroxycarboxylic acids and aromatic hydroxysulfonic acids, which may be unsubstituted or monosubstituted to tetrasubstituted by A or Hal, and Hal is F, Cl or Br and A is alkyl having from 1 to 6 carbon atoms, which may be monohalogenated to trihalogenated.

Likewise suitable are alkali metal alkoxides of the general formula $$Li^+OR^-$$

where

R is an aromatic or aliphatic carboxylic, dicarboxylic or sulfonic acid group, or is an aromatic ring selected from the group consisting of phenyl, naphthyl, anthracenyl and phenanthrenyl, which may be unsubstituted or monosubstituted to tetrasubstituted by A or Hal, or is a heterocyclic aromatic ring selected from the group consisting of pyridyl, pyrazyl and bipyridyl, which may be unsubstituted or monosubstituted to trisubstituted by A or Hal, or is an aromatic hydroxy acid selected from the group consisting of aromatic hydroxycarboxylic acids and aromatic hydroxysulfonic acids, which may be unsubstituted or monosubstituted to tetrasubstituted by A or Hal, and Hal is F, Cl or Br, and A is alkyl having from 1 to 6 carbon atoms, which may be monohalogenated to trihalogenated.

Lithium complex salts of the formula

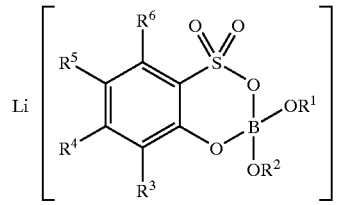

where $R^1$ and $R^2$ are identical or different, if desired are joined directly to one another by a single or double bond, and are, in each case individually or together, an aromatic ring selected from the group consisting of phenyl, naphthyl, anthracenyl and phenanthrenyl, which may be unsubstituted or monosubstituted to hexasubstituted by alkyl ($C_1$ to $C_6$), alkoxy groups ($C_1$ to $C_6$), or halogen (F, Cl, Br), or are, in each case individually or together, an aromatic heterocyclic ring selected from the group consisting of pyridyl, pyrazyl and pyrimidyl, which may be unsubstituted or monosubstituted to tetrasubstituted by alkyl ($C_1$ to $C_6$), alkoxy groups ($C_1$ to $C_6$) or halogen (F, Cl, Br), or are, in each case individually or together, an aromatic ring selected from the group consisting of hydroxybenzenecarboxyl, hydroxynaphthalenecarboxyl, hydroxybenzenesulfonyl and hydroxynaphthalenesulfonyl, which may be unsubstituted or monosubstituted to tetrasubstituted by alkyl ($C_1$ to $C_6$), alkoxy groups ($C_1$ to $C_6$) or halogen (F, Cl, Br), $R^3$-$R^6$ can, in each case individually or pairwise, if desired joined to one another directly by a single or double bond, have the following meanings:

1. Alkyl ($C_1$ to $C_6$), alkyloxy ($C_1$ to $C_6$) or halogen (F, Cl, Br)
2. an aromatic ring selected from the groups phenyl, naphthyl, anthracenyl and phenanthrenyl, which may be unsubstituted or monosubstituted to hexasubstituted by alkyl ($C_1$ to $C_6$), alkoxy groups ($C_1$ to $C_6$) or halogen (F, Cl, Br), pyridyl, pyrazyl and pyrimidyl, which may be unsubstituted or monosubstituted to tetrasubstituted by alkyl (($C_1$ to $C_6$), alkoxy groups ($C_1$ to $C_6$) or halogen (F, Cl, Br), which are prepared by the following method (DE 199 32 317)

a) 3-, 4-, 5-, 6-substituted phenol is admixed in a suitable solvent with chlorosulfonic acid, b) the intermediate from a) is reacted with chlorotrimethylsilane, filtered and fractionally distilled, c) the intermediate from b) is reacted with lithium tetramethoxyborate(1-) in a suitable solvent and the end product is isolated therefrom, may also be present in the electrolyte.

Likewise, the electrolytes may comprise compounds of the following formula (DE 199 41 566)

where

Kt=N, P, As, Sb, S, Se

A=N, P, P(O), 0, S, S(O), $SO_2$, As, As(O) Sb, Sb(O)

$R^1$, $R^2$ and $R^3$ may be identical or different and are each H, halogen, substituted and/or unsubstituted alkyl $C_nH_{2n+1}$, substituted and/or unsubstituted alkenyl having 1–18 carbon atoms and one or more double bonds, substituted and/or unsubstituted alkynyl having 1–18 carbon atoms and one or more triple bonds, substituted and/or unsubstituted cycloalkyl $C_mH_{2m-1}$, monosubstituted or polysubstituted and/or unsubstituted phenyl, substituted and/or unsubstituted heteroaryl, where A may be included in various positions in $R^1$, $R^2$ and/or $R^3$, Kt may be included in a carbocyclic or heterocyclic ring, the groups bound to Kt may be identical or different, and where n=1–18 m=3–7 k=0, 1–6 l=1 or 2 in the case of x=1 and 1 in the case of x=0 x=0, 1 y=1–4.

The process for preparing these compounds is characterized in that an alkali metal salt of the general formula

 (II)

where $D^+$ is selected from the group consisting of the alkali metals, is reacted in a polar organic solvent with a salt of the general formula

 (III)

where

Kt, A, $R^1$, $R^2$, $R^3$, k, l, x and y are as defined above and $^-$E is $F^-$, $Cl^-$, $Br^-$, $I^-$, $BF_4^-$, $ClO_4^-$, $AsF_6^-$, $SbF_6^-$ or $PF_6^-$.

It is also possible to use electrolytes comprising compounds of the general formula (DE 199 53 638)

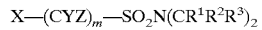

where

X is H, F, Cl, $C_nF_{2n+1}$, $C_nF_{2n-1}$, $(SO)_{2})_kN(CR^1R^2R^3)_2$

Y is H, F, Cl

Z is H, F, Cl $R^1$,$R^2$,$R^3$ is H and/or alkyl, fluoroalkyl, cycloalkyl m is 0–9 and, if X=H, m≠0 n is 1–9 k is 0 if m=0, and k=1 if m=1–9, prepared by reacting partially fluorinated or perfluorinated alkylsulfonylfluorides with dimethylamine in organic solvents, and also complex salts of the general formula (DE 199 51 804)

where:

x, y are 1, 2, 3, 4, 5, 6

$M^{x+}$ is a metal ion

E is a Lewis acid selected from the group consisting of $BR^1R^2R^3$, $AlR^1R^2R^3$, $PR^1R^2R^3R^4R^5$, $AsR^1R^2R^3R^4R^5$, $VR^1R^2R^3R^4R^5$, $R^1$ to $R^5$ are identical or different, if desired are joined directly to one another by a single or double bond, and may be, in each case individually or together, a halogen (F, Cl, Br), an alkyl or alkoxy radical ($C_1$ to $C_8$) which may be partially or fully substituted by F, Cl, Br, an aromatic ring, if desired bound via oxygen, selected from the group consisting of phenyl, naphthyl, anthracenyl and phenanthrenyl, which may be unsubstituted or monosubstituted to hexasubstituted by alkyl ($C_1$ to $C_8$) or F, Cl, Br, an aromatic heterocyclic ring, if desired bound via oxygen, selected from the group consisting of pyridyl, pyrazyl and pyrimidyl, which may be unsubstituted or monosubstituted to tetrasubstituted by alkyl (($C_1$ to $C_8$) or F, Cl, Br, and Z is $OR^6$, $NR^6R^7$, $CR^6R^7R^8$, $OSO_2R^6$, $N(SO_2R^6)(SO_2R^7)$, $C(SO_2R^6)(SO_2R^7)(SO_2R^8)$, $OCOR^6$, where $R^6$ to $R^8$ are identical or different, if desired are joined directly to one anther by a single or double bond, and are, in each case individually or together, a hydrogen or as defined for $R^1$ to $R^5$, prepared by reacting a corresponding boron or phosphorus Lewis acid-solvent adduct with a lithium or tetraalkylammonium imide, methanide or triflate.

Borate salts (DE 199 59 722) of the general formula

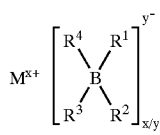

where
M is a metal ion or tetraalkylammonium ion
x, y are 1, 2, 3, 4, 5 or 6
$R^1$ to $R^4$ are identical or different alkoxy or carboxyl groups ($C_1$ to $C_8$) which may be joined directly to one another by a single or double bond may also be present. These borate salts are prepared by reacting lithium tetraalkoxyborate or a 1:1 mixture of lithium alkoxide and a boric ester in an aprotic solvent with a suitable hydroxyl or carboxyl compound in the ratio 2:1 or 4:1.

These electrolytes can be used in electrochemical cells having cathodes comprising customary lithium intercalation and insertion compounds or else cathode materials consisting of lithium mixed oxide particles and coated with one or more metal oxides (DE 199 22 522) by suspending the particles in an organic solvent, admixing the suspension with a solution of a hydrolysable metal compound and a hydrolysis solution and then filtering off, drying and, if desired, calcining the coated particles. They can also consist of lithium mixed oxide particles which are coated with one or more polymers (DE 199 46 066) and obtained by a process in which the particles are suspended in a solvent and the coated particles are subsequently filtered off, dried and, if desired, calcined.

The lithium fluoroalkylphosphates of the invention have the advantage that they display no or virtually no signs of hydrolytic decomposition over a very long period of time in the presence of water. Furthermore, they have a high thermal stability. These properties make it possible to use batteries, capacitors, supercapacitors and electrolytic cells which contain these electrolyte salts under extreme conditions, e.g. at high temperatures, without their life and performance being impaired by these conditions. Furthermore, the corresponding batteries, capacitors, supercapacitors and electrolytic cells display very good voltage constancy and unimpaired function over many charge-discharge cycles and also have low production costs.

The use of the lithium fluoroalkylphosphates of the invention in large lithium ion batteries as are used, for example, in electric road vehicles or hybrid road vehicles is likewise very advantageous, since damage to the batteries, for example in the case of an accident, even if contact with water occurs, for example due to atmospheric moisture or water used in fire fighting, results in no formation of toxic and highly corrosive hydrogen fluoride.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosures of all applications, patents and publications, cited above, and of corresponding German Application No. 10 008 955.0, filed Feb. 25, 2000, are hereby incorporated by reference.

EXAMPLE

In the following, the invention is illustrated with the aid of an example. This example serves merely to illustrate the invention and does not restrict the general scope of the invention.

Lithium tris(nonafluoro-n-butyl)trifluorophosphate

1st Step

Synthesis of tris(nonafluoro-n-butyl)difluorophosphorane

The synthesis of tris(nonafluoro-n-butyl)difluorophosphorane was carried out using a cylindrical double-walled vessel made of stainless steel and having a total volume of 1.5 liters as electrolysis cell. This electrolysis cell was provided with a nickel cathode and a nickel anode which each had an effective cathode or anode area of 15.6 $dm^2$ and a reflux condenser cooled to a temperature of −20° C. The temperature of the electrolysis cell was 0° C.

In the electrolysis cell, 1125 g of liquid hydrogen fluoride were firstly preelectrolysed for 100 hours. Subsequently, a total of 268.0 g of tributylphosphine as a 34.8 or 43.6% solution in hydrogen fluoride were added in seven portions as indicated in Table 1 below.

TABLE 1

| Amount of tributylphosphine [g] | Electrolysis time [Ah] |
| --- | --- |
| 41.8 | 0 |
| 38.0 | 291.3 |
| 38.0 | 623.8 |
| 35.1 | 930.6 |
| 41.8 | 1430.0 |
| 35.8 | 1939.0 |
| 37.5 | 2414.9 |

The electrolysis voltage was from 4.4 to 5.4 V and the current density was from 0.30 to 0.53 A/$dm^2$ at a total throughput of 2918.4 Ah (corresponding to 146.5% of theory). The liquid electrolysis products are insoluble in hydrogen fluoride and were separated from the hydrogen fluoride by phase separation. The crude product obtained in this way was then purified and isolated by fractional distillation under reduced pressure.

2nd Step

Synthesis of lithium tris(nonafluoro-n-butyl)trifluorophosphate

A suspension consisting of 0.42 g (0.016 mol) of lithium fluoride in 30 ml of a mixture of ethylene carbonate and dimethyl carbonate in a ratio of 1:1 (volume/volume) was placed in a Teflon vessel. With exclusion of moisture, 10.89 g (0.015 mol) of tris(nonafluoro-n-butyl)difluorophosphorane were added to this suspension at a temperature of from 20 to 25° C.

The resulting solution was subsequently stirred until the phase boundary initially present had disappeared and excess lithium fluoride was filtered off. The resulting solution is suitable for direct use as electrolyte in a lithium battery.

Part of the solution obtained in this way was freed of the solvent mixture under reduced pressure and the resulting lithium tris(nonafluoro-n-butyl)trifluorophosphate was characterized by means of $^{19}$F-NMR spectroscopy (Bruker, DRX-500). The $^{19}$F-NMR spectrum was recorded at a frequency of 282 MHz in deuterated acetonitrile using $CCl_3F$ as standard. The NMR-spectroscopic data and their assignments are shown in Table 2 below:

TABLE 2

| δ (ppm) | Multiplicity | Integral | Assignment |
|---|---|---|---|
| −45 | d $J_{P-F}$ = 100 Hz | 1 | P-F(axial) |
| −81 | s | 9 | $CF_3$ |
| −83 | d $J_{P-F}$ = 930 Hz | 2 | P-F(equatorial) |
| −112 | m | 6 | $CF_2$ |
| −121 | m | 6 | $CF_2$ |
| −124 | m | 6 | $CF_2$ |

COMPARATIVE EXAMPLE 1

Lithium tris(pentafluoroethyl)trifluorophosphate was prepared as described in Example 5 of DE 196 411 38.

Studies on Hydrolysis Stability

The studies on the hydrolysis stability were carried out by means of $^{19}F$- and $^{31}P$-NMR spectroscopy. The $^{19}F$-NMR spectra were recorded at a frequency of 282 MHz using $CCl_3F$ as standard. The $^{31}P$-NMR spectra were recorded at a frequency of 121 MHz using 85% $H_3PO_4$ as external standard.

For these studies, electrolyte solutions comprising, as electrolyte salt, commercially available lithium hexafluorophosphate ($LiPF_6$) (electrochemical quality), lithium tris(nonafluoro-n-butyl)trifluorophosphate ($Li[PF_3(CF_2$—$CF_2$—$CF_2$—$CF_3)_3]$) as described in Example 1 or lithium tris(pentafluoroethyl)trifluorophosphate ($Li[PF_3(CF_2CF_3)_3]$) as described in Comparative Example 1, in each case in a concentration of 0.5 [mol/kg] in a 1:1 (volume/volume) mixture of ethylene carbonate/dimethyl carbonate, were made up.

To determine the tendency of the respective lithium compound to hydrolyse, the respective electrolyte solution was admixed with 2000 ppm of water and placed in the inner capillary of a two-walled NMR tube. A small amount of a deuterated solvent and a small amount of the abovementioned standard were in each case introduced between the outer wall of the NMR tube and the inner capillary (spacing about 1 μm). The hydrolysis was then followed as a function of time by the appearance of further signals belonging to the hydrolysis products of the respective lithium compound in the respective $^{19}F$- and $^{31}P$-NMR spectra.

The results of these studies are shown in Table 3 below:

TABLE 3

| Electrolyte salt | Hydrolysis behaviour |
|---|---|
| $LiPF_6$ | Very rapid hydrolysis, further NMR signals of hydrolysis products are immediately observed |
| $Li[PF_3(CF_2CF_3)_3]$ | Slow hydrolysis, further NMR signals of hydrolysis products are observed after 10 days |
| $Li[PF_3(CF_2-CF_2-CF_2-CF_3)_3]$ | No signs of hydrolytic decomposition of the compound are observed after 4 months. |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A lithium fluoroalkylphosphate of the general formula (I), $$Li^+[PF_x(C_yF_{2y+1-z}H_z)_{6-x}]^- \qquad (I)$$

where $1 \leq x \leq 5$ $3 \leq y \leq 8$ and $0 \leq z \leq 2y+1$ and the ligands ($C_yF_{2y+1-z}H_z$) can be identical or different, with the exception of compounds of the general formula (I')

$$Li^+[PF_a(CH_bF_c(CF_3)_d)_e]^- \qquad (I')$$

in which a is an integer from 2 to 5, b=0 or 1, c=0 or 1, d=2 and e is an integer from 1 to 4, with the provisos that b and c are not simultaneously 0 or 1, and the sum of a+e is 6 and the ligands ($CH_bF_c(CF_3)_d$) can be identical or different.

2. The lithium fluoroalkylphosphate according to claim 1, wherein $1 \leq x \leq 5$, $3 \leq y \leq 8$ and z=0.

3. The lithium fluoroalkylphosphate according to claim 1, wherein the lithium fluoroalkylphosphate has the formula $$Li^+[F_{6-x}P(CF_2-CF_2-CF_3)_x]^-$$

where $1 \leq x \leq 3$ or $$Li^+[F_{6-x}P(CF_2-CF_2-CF_2-CF_3)_x]^-$$

where $1 \leq x \leq 3$.

4. The lithium fluoroalkylphosphate of the general formula (I) according to claim 1, obtained by fluorination of at least one compound of the general formula $$H_mP(C_nH_{2n+1})_{3-m} \qquad (III),$$

$$OP(C_nH_{2n+1})_3 \qquad (IV),$$

$$Cl_mP(C_nH_{2n+1})_{3-m} \qquad (V),$$

$$F_mP(C_nH_{2n+1})_{3-m} \qquad (VI),$$

$$Cl_oP(C_nH_{2n+1})_{5-o} \qquad (VII),$$

$$F_oP(C_nH_{2n+1})_{5-o} \qquad (VIII),$$

where in each case $0 \leq m \leq 2$, $3 \leq n \leq 8$ and $0 \leq o \leq 4$, by electrolysis in hydrogen fluoride, fractionation of the resulting mixture of the fluorination products by extraction, phase separation and/or distillation, and reaction of the resulting fluorinated alkylphosphorane with lithium fluoride in an aprotic solvent or solvent mixture in the absence of moisture, and purification and isolation of the resulting salt of the general formula (I).

5. The process for preparing a lithium fluoroalkylphosphate of the general formula (I) according to claim 1, wherein at least one compound of the general formula $$H_mP(C_nH_{2n+1})_{3-m} \qquad (III),$$

$$OP(C_nH_{2n+1})_3 \qquad (IV),$$

$$Cl_mP(C_nH_{2n+1})_{3-m} \qquad (V),$$

$$F_mP(C_nH_{2n+1})_{3-m} \qquad (VI),$$

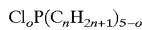

(VII),

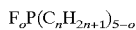

(VIII), where in each case

0≦m≦2, 3≦n≦8 and 0≦o≦4, is fluorinated by electrolysis in hydrogen fluoride, the resulting mixture of the fluorination products is fractionated by extraction, phase separation and/or distillation, and the resulting fluorinated alkylphosphorane is reacted with lithium fluoride in a aprotic solvent or solvent mixture in the absence of moisture, and the resulting salt of the general formula (I) is purified and isolated.

6. The process according to claim 5, wherein the electrolysis is carried out at a temperature of from −20 to +40° C.

7. The process according to claim 5, wherein the electrolysis is carried out at a pressure of from 0.5 to 3 bar.

8. The process according to claim 5, wherein the electrolysis is carried out at a voltage of from 4 to 6 V.

9. The process according to claim 5, wherein the electrolysis is carried out at a current density of from 0.2 to 5 A/dm².

10. The process according to claim 5, wherein the compound of the general formulae (V) and/or (VII) are reacted with at least one inorganic fluorinating agent, prior to the electrolysis in hydrogen fluoride.

11. The process according to claim 5, wherein the reaction with lithium fluoride is carried out at a temperature of from −35 to +60° C.

12. The process according to claim 5, wherein the fluorinated alkylphosphoranes are reacted with lithium fluoride in nitrites, ethers, esters, amides, sulfones or mixtures of these solvents.

13. The process according to claim 5, wherein the fluorinated alkylphosphoranes are reacted in a solvent or solvent mixture which is suitable for direct use in a primary or secondary battery, a capacitor, a supercapacitor or an electrolytic cell.

14. The process according to claim 13, wherein the solvent used is dimethyl carbonate, diethyl carbonate, propylene carbonate, ethylene carbonate, ethyl methyl carbonate, methyl propyl carbonate, 1,2-dimethoxyethane, 1,2-diethoxyethane, methyl acetate, γ-butyrolactone, ethyl acetate, methyl propionate, ethyl propionate, methyl butyrate, ethyl butyrate, dimethyl sulfoxide, dioxolane, sulfolane, acetonitrile, acrylonitrile, tetrahydrofuran, 2-methyltetrahydrofuran or a mixture thereof.

15. A lithium fluoroalkylphosphate obtained by the process according to claim 5.

16. A primary battery, secondary battery, capacitor, supercapacitor or electrolytic cell, comprising an electrolyte salt having at least one lithium fluoroalkylphosphate according to claim 1.

17. An electrolyte for primary batteries, secondary batteries, capacitors, supercapacitors and/or electrolytic cells comprising at least one lithium fluoroalkylphosphate according to claim 1.

18. An electrolyte according to claim 17, wherein the concentration of lithium fluoroalkylphosphate in the electrolyte is from 0.01 to 3 mol/l.

19. An electrolyte according to claim 17, wherein the concentration of lithium fluoroalkylphosphate in the electrolyte is from 0.01 to 2 mol/l.

20. An electrolyte according to claim 17, wherein the concentration of lithium fluoroalkylphosphate in the electrolyte is from 0.1 to 1.5 mol/l.

21. The process according to claim 5, wherein the electrolysis is carried out at a temperature of 5–+5° C.

22. The process according to claim 5, wherein the electrolysis is carried out under atmospheric pressure.

23. The process according to claim 5, wherein the electrolysis is carried out at a voltage of 4.5–5.5 volt.

24. The process according to claim 5, wherein the electrolysis is carried out at a current density of 0.5–1.5 A/dm².

25. The process according to claim 10, wherein the at least one inorganic fluorinating agent is $SbF_3$, $SbF_5$, $MoF_5$, $VF_5$ or a mixture thereof.

26. The process according to claim 5, wherein the reaction with lithium fluoride is carried out at a temperature of −10–25° C.

* * * * *